(12) United States Patent
Bagchi et al.

(10) Patent No.: US 9,259,394 B2
(45) Date of Patent: Feb. 16, 2016

(54) PARTIAL DIP COATING OF DOSAGE FORMS FOR MODIFIED RELEASE

(75) Inventors: Saumitra Bagchi, Princeton, NJ (US); Murali Vuppala, Collegeville, PA (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 364 days.

(21) Appl. No.: 12/961,862

(22) Filed: Dec. 7, 2010

(65) Prior Publication Data

US 2011/0135694 A1 Jun. 9, 2011

Related U.S. Application Data

(60) Provisional application No. 61/267,137, filed on Dec. 7, 2009.

(51) Int. Cl.

| | |
|---|---|
| *A61K 9/00* | (2006.01) |
| *A61K 9/28* | (2006.01) |
| *A61K 31/137* | (2006.01) |
| *A61K 31/167* | (2006.01) |
| *A61K 31/192* | (2006.01) |
| *A61K 9/20* | (2006.01) |

(52) U.S. Cl.
CPC ............. *A61K 9/284* (2013.01); *A61K 9/2072* (2013.01); *A61K 9/2893* (2013.01); *A61K 31/137* (2013.01); *A61K 31/167* (2013.01); *A61K 31/192* (2013.01); *A61K 9/2027* (2013.01); *A61K 9/2054* (2013.01); *A61K 9/2059* (2013.01)

(58) Field of Classification Search
None
See application file for complete search history.

(56) References Cited

U.S. PATENT DOCUMENTS

| | | | |
|---|---|---|---|
| 4,756,911 A * | 7/1988 | Drost et al. .................... | 424/468 |
| 4,801,461 A | 1/1989 | Hamel et al. | |
| 4,839,177 A * | 6/1989 | Colombo et al. ............. | 424/482 |
| 4,857,330 A | 8/1989 | Stephens et al. | |
| 4,865,849 A | 9/1989 | Conte et al. | |
| 5,186,937 A | 2/1993 | Sparks et al. | |
| 5,464,633 A | 11/1995 | Conte et al. | |
| 5,830,501 A | 11/1998 | Dong et al. | |
| 6,113,945 A | 9/2000 | Jacobs et al. | |
| 6,126,767 A | 10/2000 | Smith et al. | |
| 6,787,156 B1 | 9/2004 | Bar-Shalom | |
| 6,838,094 B2 * | 1/2005 | Grimmett et al. ............. | 424/474 |
| 6,893,661 B1 * | 5/2005 | Odidi et al. .................... | 424/468 |
| 2003/0070584 A1 | 4/2003 | Gulian et al. | |
| 2003/0219484 A1 * | 11/2003 | Sowden et al. ............... | 424/473 |
| 2003/0232083 A1 * | 12/2003 | Wynn et al. ................... | 424/473 |
| 2004/0213849 A1 * | 10/2004 | Sowden et al. ............... | 424/472 |
| 2006/0099245 A1 * | 5/2006 | Kumar et al. ................. | 424/451 |
| 2007/0202050 A1 * | 8/2007 | Berry et al. ..................... | 424/45 |
| 2008/0166407 A1 | 7/2008 | Shalaby et al. | |

FOREIGN PATENT DOCUMENTS

| | | |
|---|---|---|
| EP | 0206890 A2 | 12/1986 |
| EP | 0274734 A1 | 7/1988 |
| EP | 0788790 A2 | 8/1997 |
| WO | WO 99/62496 A1 | 12/1999 |
| WO | WO 01/56550 A1 | 8/2001 |
| WO | WO 03/020246 A1 | 3/2003 |
| WO | WO 2006/031584 A2 | 3/2006 |

OTHER PUBLICATIONS

PCT International Search Report for PCT/US2010/059228 dated May 27, 2011.
Lachman, L., et al., *The Theory and Practice of Industrial Pharmacy*, 3rd Ed., p. 293-342, 1986.
Ratner, Buddy D., et al., Hydrogels for Medical and Related Applications, *ACS Symposium Series*, No. 31, p. 1-38, 1976 published by The American Chemical Society.
Schact, Etienne H., *Recent Advances in Drug Delivery Systems*, p. 259-278 published by Plenum Press, NY, 1982.

* cited by examiner

*Primary Examiner* — Brian Gulledge
(74) *Attorney, Agent, or Firm* — Laura A. Donnelly (57) ABSTRACT

A dosage form comprising a tablet core containing at least one active ingredient and having at least one modified release coating that partially surrounds the tablet core is disclosed. The tablet core is preferably in the form of a compressed core wherein the at least one modified release coating is provided on a position of the exterior surface of the compressed core using dipping technology. The invention also relates to a method of manufacturing the dosage form and a method of treatment using the dosage form.

17 Claims, 8 Drawing Sheets

PARTIAL DIP COATING OF DOSAGE FORMS FOR MODIFIED RELEASE

CROSS REFERENCE TO RELATED APPLICATIONS

This application claims priority from U.S. Provisional Application Ser. No. 61/267,137, filed on Dec. 7, 2009 entitled "PARTIAL DIP COATING OF DOSAGE FORMS FOR MODIFIED RELEASE", the contents of each of which are hereby incorporated by reference in their entirety.

FIELD OF THE INVENTION

The present invention relates to a dosage form comprising a tablet core containing at least one active ingredient and having at least one modified release coating that partially surrounds the tablet core. The tablet core is preferably in the form of a compressed core wherein at least one modified release coating is provided on a portion of the exterior surface of the compressed core using dipping technology. The invention also relates to a method of manufacturing the dosage form and a method of treatment using the dosage form.

BACKGROUND OF THE INVENTION

Modified release pharmaceutical dosage forms have long been used to optimize drug delivery and enhance patient compliance, especially by reducing the number of doses of medicine the patient must take in a day. In some instances, it is also desirable for a dosage form to deliver more than one drug at different rates or times. Modified release dosage forms should ideally be adaptable so that release rates and profiles can be matched to physiological requirements. Because the onset and duration of the therapeutic efficacy of drugs vary widely, as do their absorption, distribution, metabolism, and elimination, it is often desirable to modify the release of different drugs in different ways, or to have a first dose of drug immediately released from the dosage form, while a second dose of the same or a different drug is released in a modified, e.g., delayed, pulsatile, repeat action, controlled, pH dependent, sustained, prolonged, extended, or retarded manner.

Well known mechanisms by which a dosage form can deliver drug at a controlled rate include permeation, diffusion, erosion, and osmosis. It is often practical to design dosage forms that use a combination of the above mechanisms to achieve a particularly desirable release profile for a particular active ingredient.

An important objective of modified release dosage forms is to provide a desired blood concentration versus time (pharmacokinetic, or PK) profile for the drug. Fundamentally, the PK profile for a drug is dependent on the rate of absorption of the drug into the blood, and the rate of elimination of the drug from the blood. To be absorbed into the blood (circulatory system), the drug must first be dissolved in the gastrointestinal fluids. For those relatively rapidly absorbed drugs whose dissolution in the gastrointestinal fluids is the rate limiting step in drug absorption, controlling the rate of dissolution (i.e., drug release from the dosage form) allows the formulator to control the rate of drug absorption into the circulatory system of a patient. The type of PK profile, and correspondingly, the type of dissolution or release profile desired, depends on, among many other factors, the particular active ingredient and physiological condition being treated.

One particularly desirable PK profile is achieved by a dosage form that delivers a delayed release dissolution profile, in which the release of one or more doses of drug from the dosage form is delayed for a pre-determined time after contacting of the dosage form by a liquid medium, such as for example, by the gastro-intestinal fluid after ingestion by the patient. The delay period ("lag time") can be followed either by prompt release of the active ingredient ("delayed burst"), or by sustained (prolonged, extended, or retarded) release of the active ingredient ("delayed then sustained"). U.S. Pat. No. 5,464,633 to Jagotec, for example, discloses delayed-release dosage forms consisting of a core containing an active and polymeric substances and an external layer completely coating the core in which the external coating layer is applied by a compression coating process.

One particularly desirable type of delayed release PK profile is obtained from a "pulsatile" release profile, in which for example, a first dose of a drug is delivered, followed by a delay period ("lag time") during which there is substantially no release of the drug from the dosage form, followed by either prompt or sustained release of a subsequent dose of the same drug. In one particularly desirable type of pulsatile drug delivery system, the first dose is released essentially immediately upon contacting of the dosage form with a liquid medium, and the delay period corresponds approximately to the time during which a therapeutic concentration of the first dose is maintained in the blood. Pulsatile delivery systems are particularly useful for applications where a continuous release of drug is not ideal. Examples of this are drugs exhibiting first pass metabolism by the liver, drugs that induce biological tolerance, i.e., the therapeutic effect decreases with continuous presence of the drug at the site of action, and drugs whose efficacy is influenced by circadian rhythms of body functions or disease. One typical pulsatile dosage form design contains the first dose of drug in an exterior coating, or shell, while subsequent doses of drug are contained in underlying layers of subcoatings, or a central core. Pulsatile dosage forms may deliver an active ingredient in a pH dependent or pH independent manner. pH dependent types of dosage forms typically deliver the active ingredient through the addition of a pH dependent polymer, such as an enteric or reverse-enteric polymer.

PCT Publication No. WO99/62496 to Alza, for example, discloses a dosage form comprising an immediate-release dose of drug contained within an overcoat applied onto a surface of a semi-permeable coating of an osmotic dosage form. U.S. Pat. Nos. 4,857,330 and 4,801,461 to Alza disclose dosage forms comprising an exterior drug coat that surrounds a semi-permeable wall, which in turn surrounds an internal compartment containing a second dose of drug, and comprises exit means for connecting the interior of the dosage form with the exterior environment of use. These dosage forms are designed to release drug immediately from the exterior coating, followed by a relatively short delay period, followed by a sustained release of drug from the internal compartment.

U.S. Pat. No. 4,865,849 to Pharmidea discloses a tablet that releases active substances at successive times, comprising a first layer containing a portion of the active substance, a water soluble or water gellable barrier layer, and a third layer containing the remaining portion of active substance, wherein the barrier layer and the third layer are in an insoluble, low-permeable casing. The casing can be applied by various methods such as spraying, compression, or immersion, or the tablet parts can be inserted into a pre-formed casing. These systems suffer from the complexity and high cost of assembling multiple, separate compartments comprising multiple, different compositions.

U.S. Pat. No. 4,839,177 to Jagotec, discloses a system for the controlled release of active substances, consisting of: (a) a deposit-core; and (b) a support-platform applied to the deposit-core. The deposit-core contains active substance and a polymeric material having a high degree of swelling on contact with water or aqueous liquids, a gellable polymeric material, and other adjuvants able to provide the mixture with suitable characteristics for its compression and for its intake of water.

U.S. Pat. No. 6,126,767 to Perrigo, discloses a capsule medicament consisting of a solid core covered with two shrink-wrapped, hard-shell gelatin capsule halves. The solid core is covered with the hard-shell gelatin capsule halves by individually shrink-wrapping onto first one end of the core a first hard-shell gelatin capsule half and then individually shrink-wrapping onto a second end of the core a second hard-shell gelatin capsule half. The capsule medicament is designed for immediate release of the active ingredient.

U.S. Pat. No. 6,113,945 to Perrigo, discloses a caplet or tablet core with a clear or single color uniform covering that is applied either through an enrobing process, by spraying or by a single dip-coating step. The core itself can have a first color or be colorless, and its clear or single color covering has the outer surface of one end or one side colored by a dye to provide a two-color appearance. The dye can be applied by dipping or spray painting with a jet-spraying apparatus.

U.S. Pat. No. 6,787,156 to BM Research discloses a composition for controlled delivery of at least one active substance comprising a first cellulose derivative which has thermoplastic properties and which is substantially insoluble in an aqueous medium in which the composition is to be used, and at least one of a second cellulose derivative which is soluble or dispersible in water, a plasticizer, and a filler.

U.S. Patent Publication No. 20030070584 to McNeil discloses a water soluble, gelatin-free dip coating for pharmaceutical solid dosage forms such as tablets comprising HPMC and xanthan gum, carrageenan, and mixtures thereof, or HPMC and castor oil or maltodextrin.

U.S. Patent No. 20080166407 to Shalaby et al. discloses multifunctional, single, bilayer, and trilayer coated tablets for combination therapy wherein the bioactive agents responsible for the therapeutic multifunctionality are present as a combination of a gastric acid-reducing agent, such as omeprazole and ranitidine, and at least one analgesic/anti-inflammatory agent, such as acetaminophen, naproxen sodium, ibuprofen, tolmetin, and aspirin.

All references cited are incorporated by reference in their entirety herein.

Coating methods such as those described above have inherent disadvantages, including long processing times, limited ability to allow functional placement of coatings, or multiple coating steps in order to provide multiple release rates (as in spray coatings), thick coatings which can affect swallowability and limit types of release rates (such as compression coatings), or the use of laser drilling equipment (such as osmotic coatings).

There is a need in the art for improved dosage forms for providing modified release of active ingredient.

SUMMARY OF THE INVENTION

It is an object of the invention to provide a method of preparing a modified release dosage form wherein the functional modified release coating is applied by the use of dipping technology, wherein the release rate of the active ingredient in the core is customized by varying the length of the dip coat on the long (i.e., latitudinal) axis.

It is another object of the invention to provide a dosage form with immediate release and modified release portions in the tablet manufactured by application of release controlling coating on the modified release portion. Such a core does not require multiple pieces (as in a muticore form) or multilayers (as in a bilayer or trilayer core).

Controlled release dosage forms provide many advantages over immediate release dosage forms. The invention involves partially coating a tablet with a semi-permeable or a low-permeable coating to a predetermined height using an aqueous or a non-aqueous solution of a polymer and air drying the tablet. The uncoated portion of the tablet releases the drug immediately and the portion of the tablet that is coated releases the drug slowly as the tablet surface that is exposed to the medium is reduced to the cross sectional area of the tablet. As the drug is released from the core in the coated portion of the tablet, dissolution medium has to travel deep into the tablet coated with polymer shell to dissolve the drug and release it to the medium.

The modified release tablets of the invention, which are simpler and potentially more cost effective than sustained release tablets that utilize multiple spray coating steps, or particulate coatings, provide users with convenience and lower doses. Convenience is provided during the manufacturing process as the dipped coatings of the present invention allow for a single application of coating. The dip coatings of the invention also involve reduced cost as a great amount of cost lies in the processing time involved with applying multiple coatings to a tablet, as in spray coating or osmotic coating.

The dipped dosage forms of the invention exhibit modified release of one or more active ingredients contained therein. The active ingredient or ingredients may be found within the core. As used herein, the term "modified release" shall apply to dosage forms, coatings, shells, cores, portions thereof, or compositions that alter the release of an active ingredient in any manner. The active ingredient or ingredients that are released in a modified manner may be contained within the coating, shell, core, composition, or portion thereof providing the modification. Alternatively the modified release active ingredient may be contained in a different portion of the dosage form from the coating, shell, core, composition, or portion thereof providing the modification; for example the modified release active ingredient may be contained in a core portion, and the modification may be provided by the overlaying shell portion. Types of modified release include controlled, prolonged, sustained, extended, delayed, pulsatile, repeat action, and the like. Suitable mechanisms for achieving these types of modified release include diffusion, erosion, surface area control via geometry and/or low-permeable barriers, or other mechanisms known in the art. Moreover, modified release properties of the dosage form may be achieved through design of the core or a portion thereof, or of the coating or portions of the coating, or a combination of these parts of the dosage form.

The dissolution profile of each active ingredient from the dosage form may be governed by a sum of contributions from the properties of the various portions. Additionally, a single portion, for example a core portion, may possess a combination of erosional and diffusional properties. In any case, the dissolution rate of a particular active ingredient from the dosage form will be the sum of the contributions from all the various mechanisms contributed by the various portions of the dosage form which effect the release of that particular active ingredient, as depicted by the following equation:

$$\text{Rate}_{total} \ldots = \ldots X_1 \text{Rate}_1 \ldots + X_2 \text{Rate}_2 \ldots + X_3 \text{Rate}_3 \ldots + X_n \text{Rate}_n$$

where $X_1$, $X_2$, $X_3$, ... $X_n$ are the relative contribution fractions of the total release rate, and $Rate_1$, $Rate_2$, $Rate_3$, ... $Rate_n$ are the various release rates contributed by effects of the various portions of the dosage form on a particular active ingredient.

Another particularly desirable PK profile is achieved by a dosage form that delivers a delayed release dissolution profile, in which the release of one or more doses of drug from the dosage form is delayed for a pre-determined time after contact with a liquid medium, e.g., upon ingestion by the patient. The delay period ("lag time") can be followed either by prompt release of the active ingredient ("delayed burst"), or by sustained (prolonged, extended, or retarded) release of the active ingredient ("delayed then sustained").

One particularly desirable type of delayed release PK profile, is a "pulsatile" profile in which, for example, a first dose of a first drug is delivered, followed by a delay period during which there is substantially no release of the first drug from the dosage form, followed by either prompt or sustained release of a subsequent dose of the same drug. In one particularly desirable type of pulsatile drug delivery system, the first dose is released essentially immediately upon contacting of the dosage form with a liquid medium. In another particularly desirable type of pulsatile drug delivery system, the delay period corresponds approximately to the time during which a therapeutic concentration of the first dose is maintained in the blood. Pulsatile delivery systems are particularly useful for applications where a continuous release of drug is not ideal. Examples of this are drugs exhibiting first pass metabolism by the liver, drugs that induce biological tolerance (i.e., the therapeutic effect decreases with continuous presence of the drug at the site of action), and drugs whose efficacy is influenced by circadian rhythms of body functions or diseases.

According to an embodiment, the dosage form is a tablet that is partially dip coated on both sides of the tablet leaving the central band uncoated.

According to another embodiment, the dosage form is a tablet having a portion that is partially dip coated with low-permeable coating and another portion of the tablet is dip coated with a semi-permeable coating.

The coating may contain coating polymers applied from a solvent based solution or from a latex based aqueous dispersion (typically with the addition of a plasticizer).

The dosage form which includes the modified release tablets of the invention provide the blood levels quickly with active in order to provide quick relief and with sustained levels of active over time to provide continued relief.

The dosage form which includes the modified release tablets of the invention may contain a single active or more than one active and/or may treat a single indication or multiple indications and/or a single symptom or multiple symptoms.

The dosage form which includes the modified release tablets of the invention can provide zero and/or first order release.

The invention also relates to a method of manufacturing the dosage form and a method of treatment using the dosage form.

DETAILED DESCRIPTION OF THE INVENTION

As used herein, the term "dosage form" applies to any solid object, semi-solid, or liquid-filled composition designed to contain a specific pre-determined amount (dose) of a certain ingredient, for example, an active ingredient as defined below. Suitable dosage forms may be pharmaceutical drug delivery systems, including those for oral administration, buccal administration, rectal administration, topical or mucosal delivery, or subcutaneous implants, or other implanted drug delivery systems; or compositions for delivering minerals, vitamins and other nutraceuticals, oral care agents, flavorants, and the like. Preferably the dosage forms of the present invention are considered to be solid, however they may contain liquid or semi-solid components. In a particularly preferred embodiment, the dosage form is an orally administered system for delivering a pharmaceutical active ingredient to the gastro-intestinal tract of a human.

Suitable "active ingredients" for use in this invention include for example pharmaceuticals, minerals, vitamins and other nutraceuticals, oral care agents, flavorants and mixtures thereof. Suitable pharmaceuticals include analgesics, anti-inflammatory agents, antiarthritics, anesthetics, antihistamines, antitussives, antibiotics, anti-infective agents, antivirals, anticoagulants, antidepressants, antidiabetic agents, antiemetics, antiflatulents, antifungals, antispasmodics, appetite suppressants, bronchodilators, cardiovascular agents, central nervous system agents, central nervous system stimulants, decongestants, oral contraceptives, diuretics, expectorants, gastrointestinal agents, migraine preparations, motion sickness products, mucolytics, muscle relaxants, osteoporosis preparations, polydimethylsiloxanes, respiratory agents, sleep-aids, urinary tract agents and mixtures thereof.

Suitable oral care agents include breath fresheners, tooth whiteners, antimicrobial agents, tooth mineralizers, tooth decay inhibitors, topical anesthetics, mucoprotectants, and the like.

Suitable flavorants include menthol, peppermint, mint flavors, fruit flavors, chocolate, vanilla, bubblegum flavors, coffee flavors, liqueur flavors and combinations and the like.

Examples of suitable gastrointestinal agents include antacids such as calcium carbonate, magnesium hydroxide, magnesium oxide, magnesium carbonate, aluminum hydroxide, sodium bicarbonate, dihydroxyaluminum sodium carbonate; stimulant laxatives, such as bisacodyl, cascara sagrada, danthron, senna, phenolphthalein, aloe, castor oil, ricinoleic acid, and dehydrocholic acid, and mixtures thereof; H2 receptor antagonists, such as famotadine, ranitidine, cimetadine, nizatidine; proton pump inhibitors such as omeprazole or lansoprazole; gastrointestinal cytoprotectives, such as sucraflate and misoprostol; gastrointestinal prokinetics, such as prucalopride, antibiotics for *H. pylori*, such as clarithromycin, amoxicillin, tetracycline, and metronidazole; antidiarrheals, such as diphenoxylate and loperamide; glycopyrrolate; antiemetics, such as ondansetron, analgesics, such as mesalamine A preferred gastrointestinal agent is omeprazole.

In one embodiment of the invention, the active ingredient may be selected from bisacodyl, famotadine, ranitidine, cimetidine, prucalopride, diphenoxylate, loperamide, lactase, mesalamine, bismuth, antacids, and pharmaceutically acceptable salts, esters, isomers, and mixtures thereof.

In another embodiment, the active ingredient is selected from analgesics, anti-inflammatories, and antipyretics, e.g., non-steroidal anti-inflammatory drugs (NSAIDs), including propionic acid derivatives, e.g., ibuprofen, naproxen, ketoprofen and the like; acetic acid derivatives, e.g., indomethacin, diclofenac, sulindac, tolmetin, and the like; fenamic acid derivatives, e.g., mefanamic acid, meclofenamic acid, flufenamic acid, and the like; biphenylcarbodylic acid derivatives, e.g., diflunisal, flufenisal, and the like; and oxicams, e.g., piroxicam, sudoxicam, isoxicam, meloxicam, and the like. In one particular embodiment, the active ingredient is selected from propionic acid derivative NSAID, e.g., ibuprofen, naproxen, flurbiprofen, fenbufen, fenoprofen, indoprofen, ketoprofen, fluprofen, pirprofen, carprofen, oxaprozin, pranoprofen, suprofen, and pharmaceutically acceptable salts, derivatives, and combinations thereof. In another particular embodiment of the invention, the active ingredient may be selected from acetaminophen, acetyl salicylic acid, ibuprofen, naproxen, ketoprofen, flurbiprofen, diclofenac, cyclobenzaprine, meloxicam, rofecoxib, celecoxib, and pharmaceutically acceptable salts, esters, isomers, and mixtures thereof. A preferred (analgesic) is acetaminophen.

In another embodiment of the invention, the active ingredient may be selected from upper respiratory agents, such as pseudoephedrine, phenylephrine, guaifensin, phenylpropanolamine, chlorpheniramine, dextromethorphan, diphenhydramine, astemizole, terfenadine, fexofenadine, loratadine, desloratadine, cetirizine, mixtures thereof and pharmaceutically acceptable salts, esters, isomers, and mixtures thereof. A preferred upper respiratory agent is phenylephrine HCl. Another preferred upper respiratory agent is guaifensin.

The active ingredient or ingredients are present in the dosage form in a therapeutically effective amount, which is an amount that produces the desired therapeutic response upon oral administration and can be readily determined by one skilled in the art. In determining such amounts, the particular active ingredient being administered, the bioavailability characteristics of the active ingredient, the dosing regimen, the age and weight of the patient, and other factors must be considered, as known in the art. Typically, the dosage form comprises at least about 1 weight percent, for example, the dosage form comprises at least about 5 weight percent, say at least about 20 weight percent, of a combination of one or more active ingredients. In one embodiment, a core comprises a total of at least about 25 weight percent (based on the weight of the core) of one or more active ingredients.

The active ingredient or ingredients may be present in the dosage form in any form. For example, the active ingredient may be dispersed at the molecular level, e.g., melted or dissolved, within the dosage form, or may be in the form of particles, which in turn may be coated or uncoated. If an active ingredient is in the form of particles, the particles (whether coated or uncoated) typically have an average particle size of about 1-2000 microns. In one preferred embodiment, such particles are crystals having an average particle size of about 1-300 microns. In another preferred embodiment, the particles are granules or pellets having an average particle size of about 50-2000 microns, preferably about 50-1000 microns, most preferably about 100-800 microns.

Each core may be any solid form. As used herein, "core" refers to a material which is at least partially enveloped or surrounded by another material and has a thickness of at least about 2 mm to about 30 mm. Preferably, a core is a self-contained unitary object, such as a "tablet", which is a compressed or molded solid dosage form of any size or shape. Solid, generally oblong-shaped tablets may sometimes be referred to as "caplets".

The cores may be prepared by any suitable method, including for example compression or molding, and depending on the method by which they are made, typically comprise active ingredient and a variety of excipients.

In embodiments in which the core is made by compression, suitable excipients include fillers, binders, disintegrants, lubricants, glidants, and the like, as known in the art.

Suitable fillers for use in making a core or core portion by compression include water-soluble compressible carbohydrates such as sugars, which include dextrose, sucrose, maltose, and lactose, sugar-alcohols, which include mannitol, sorbitol, maltitol, xylitol, starch hydrolysates, which include dextrins, and maltodextrins, and the like, water insoluble plastically deforming materials such as microcrystalline cellulose or other cellulosic derivatives, water-insoluble brittle fracture materials such as dicalcium phosphate, tricalcium phosphate and the like and mixtures thereof.

Suitable binders for making a core or core portion by compression include dry binders such as polyvinyl pyrrolidone, hydroxypropylcellulose, hydroxypropylmethylcellulose, and the like; wet binders such as water-soluble polymers, including hydrocolloids such as acacia, alginates, agar, guar gum, locust bean, carrageenan, carboxymethylcellulose, tara, gum arabic, tragacanth, pectin, xanthan, gellan, gelatin, maltodextrin, galactomannan, pusstulan, laminarin, scleroglucan, inulin, whelan, rhamsan, zooglan, methylan, chitin, cyclodextrin, chitosan, polyvinyl pyrrolidone, cellulosics, sucrose, starches, and the like; and derivatives and mixtures thereof.

Suitable disintegrants for making a core or core portion by compression, include sodium starch glycolate, cross-linked polyvinylpyrrolidone, cross-linked carboxymethylcellulose, starches, microcrystalline cellulose, crospovidone and the like.

Suitable lubricants for making a core or core portion by compression include long chain fatty acids and their salts, such as magnesium stearate and stearic acid, talc, glycerides and waxes.

Suitable colorants include lakes, dyes, and opacifiers, including metal containing lakes such as aluminum, magnesium and calcium lakes. Specific opacifiers include but are not limited to titanium dioxide.

Suitable glidants for making a core or core portion by compression, include colloidal silicon dioxide, and the like.

Suitable pH-dependent polymers for use as release-modifying excipients for making a core or core portion by compression include enteric cellulose derivatives, for example hydroxypropyl methylcellulose phthalate, hydroxypropyl methylcellulose acetate succinate, cellulose acetate phthalate; natural resins such as shellac and zein; enteric acetate derivatives such as for example polyvinylacetate phthalate, cellulose acetate phthalate, acetaldehyde dimethylcellulose acetate; and enteric acrylate derivatives such as for example polymethacrylate-based polymers such as poly(methacrylic acid, methyl methacrylate) 1:2, which is commercially available from Rohm Pharma GmbH under the tradename EUDRAGIT S, and poly(methacrylic acid, methyl methacrylate) 1:1, which is commercially available from Rohm Pharma GmbH under the tradename EUDRAGIT L, and the like, and derivatives, salts, copolymers, and combinations thereof. In one embodiment a pH dependent polymer is applied to the core containing the active ingredient in a first coating step. In one embodiment this first coating step substantially surrounds the core. As defined herein, "substantially surrounds" includes covering at least 95%, e.g., at least 99% of the surface area of the core. This first coating step may be applied by any method; including spraying, compression coating, enrobing or dipping.

In another embodiment a subcoat is applied in the first coating step. The subcoat may comprise a modified release coating, an immediate release coating, or a pH dependent coating.

Suitable materials for use as the immediate release coating include polyvinylalcohol (PVA); water soluble polycarbohydrates such as hydroxypropyl starch, hydroxyethyl starch, pullulan, methylethyl starch, carboxymethyl starch, pre-gelatinized starches, and film-forming modified starches; water swellable cellulose derivatives such as hydroxypropyl cellulose (HPC), hydroxypropylmethyl cellulose (HPMC), methyl cellulose (MC), hydroxyethylmethylcellulose (HEMC), hydroxybutylmethylcellulose (HBMC), hydroxyethylethylcellulose (HEEC), and hydroxyethylhydroxypropylmethyl cellulose (HEMPMC); water soluble copolymers such as methacrylic acid and methacrylate ester copolymers, polyvinyl alcohol and polyethylene glycol copolymers, polyethylene oxide and polyvinylpyrrolidone copolymers; and derivatives and combinations thereof.

In certain embodiments, the degree to which the modified release dipped coating is applied to the core will regulate the rate and amount of active ingredient which is dispersed into the gastrointestinal media upon ingestion. The amount of dipped portion will be dependent of the amount of active ingredient in the core, the amount of active ingredient which is desired for immediate release versus modified release, and the type of modified release. In one embodiment the dipped portion is applied at about 10 percent, up to about 25 percent, up to about 50 percent, up to about 75 percent up to about 90 percent, up to about 95 percent of the surface area of the core portion. In one embodiment, the core is a caplet and the dipped portion circumscribes the longitudinal axis of the core such that the dipped portion can easily be modified to regulate release. In one embodiment a top and bottom portion of a tablet are dipped with the modified release coating and the center portion is exposed for immediate release of the active ingredient.

In one embodiment the tablet is held or gripped in a holder which is designed to mask the portion of the tablet which is not coated upon dipping, in order to precisely apply the appropriate amount of the modified release coating.

The thickness of the dipped coating portion may be adjusted by adjusting the viscosity of the dipping solution, and by adjusting the level of solids in solution. The solids of the coating solution may be from about 2 percent solids to about 50 percent solids, preferably from about 5 percent to about 25 percent solids.

In one embodiment the core is a multilayer tablet. Multilayer tablets may be employed in order to separate incompatible active ingredients, or to further modify the release rate of the at least one active ingredient. In one embodiment the multilayer tablet is a bilayer tablet, which comprises one active ingredient in the first layer and a second active ingredient or a second portion of the first active ingredient in the second layer. The first layer portion may be coated with a dipped portion or uncoated (i.e., exposed) with the dipped portion and the second layer portion may be coated with the dipped portion. In one embodiment the first layer portion is an immediate release portion.

The dipping coating solution may be applied via a solvent based or an aqueous based solution. Suitable solvents may be employed in order to dissolve the modified release agents or polymers, and include but are not limited to ethanol, methanol, isopropanol, acetone, methylene chloride and hexane(s).

In one embodiment the dipped portion contains a pore forming agent in order to create a semi-permeable coating. As used herein, the term "semi-permeable" means permeable to the passage of water but not permeable to the passage of active ingredient therethrough. The semi-permeable dipped portion allows water to be absorbed therethrough and into the core of the dosage form from the environment, such as the dissolution media or gastro-intestinal fluids. The semi-permeable dipped portion functions as a barrier to the passage of active ingredient from the underlying core portion, forcing the active ingredient to be released from the dosage form via a different avenue, such as an orifice or passageway, or through a diffusible dipped coating portion. The semi-permeable dipped coating portions are non-erodible, and they are insoluble in fluids. Suitable pore forming agents include but are not limited to crystalline materials such as sugars and salts, or water soluble polymers such as but not limited to hypromellose, hydroxypropylcellulose, polyethylene glycol, and methylcellulose.

Suitable pharmaceutically acceptable adjuvants for making a core or core portion by compression include, preservatives; high intensity sweeteners such as aspartame, acesulfame potassium, sucralose, and saccharin; flavorants; colorants; antioxidants; surfactants; wetting agents; and the like and mixtures thereof.

In embodiments wherein the core is prepared by compression, a dry blending (i.e., direct compression), or wet granulation process may be employed, as known in the art. In a dry blending (direct compression) method, the active ingredient or ingredients, together with the excipients, are blended in a suitable blender, then transferred directly to a compression machine for pressing into tablets. In a wet granulation method, the active ingredient or ingredients, appropriate excipients, and a solution or dispersion of a wet binder (e.g., an aqueous cooked starch paste, or solution of polyvinyl pyrrolidone) are mixed and granulated. Alternatively a dry binder may be included among the excipients, and the mixture may be granulated with water or other suitable solvent. Suitable apparatuses for wet granulation are known in the art, including low shear, e.g., planetary mixers; high shear mixers; and fluid beds, including rotary fluid beds. The resulting granulated material is dried, and optionally dry-blended with further ingredients, e.g., adjuvants and/or excipients such as for example lubricants, colorants, and the like. The final dry blend is then suitable for compression. Methods for direct compression and wet granulation processes are known in the art, and are described in detail in, for example, Lachman, et al., The Theory and Practice of Industrial Pharmacy, Chapter 11 (3rd ed. 1986).

The dry-blended, or wet granulated, powder mixture is typically compacted into tablets using a rotary compression machine as known in the art.

In certain other embodiments, one or more core portions function as a diffusional matrix. In these embodiments, the core portion preferably comprises active ingredient, distributed throughout an insoluble porous matrix, which contains pores or channels through which fluids can enter the core portion, and the active ingredient must diffuse to be released from the dosage form. In these embodiments, the rate of active ingredient release from the core portion will depend upon the area (A) of the matrix, the diffusion coefficient (D), the porosity (E) and tortuosity (T) of the matrix, the drug solubility (Cs) in the dissolution medium, and the drug concentration (Cp) in the dosage form. In preferred embodiments in which a core portion functions as a diffusional matrix, the release of the active ingredient from the core portion may be described as controlled, prolonged, sustained, or extended. In these embodiments, the contribution to active ingredient dissolution from the subject core portion may follow zero-order, first-order, or preferably square-root of time kinetics. In certain such embodiments, the diffusional matrix core portion preferably comprises a pore former.

In one embodiment the dipped coating portion comprises at least one water insoluble polymer. Examples of suitable water-insoluble polymers include ethylcellulose, polyvinyl alcohols, polyvinyl acetate, polycaprolactones, cellulose acetate and its derivatives, cellulose acylate, cellulose diacylate, cellulose triacylate, cellulose acetate, cellulose diacetate, cellulose triacetate acrylates, methacrylates, acrylic acid copolymers; and the like and derivatives, copolymers, and combinations thereof.

In one embodiment, the dipped coating portion comprises at least one aqueous polymer. Examples of suitable aqueous polymers include hydroxypropylcellulose (HPC), hypromellose, methylcellulose, povidone, and polyvinylalcohol (PVA). Aqueous polymers further include water soluble polycarbohydrates such as hydroxypropyl starch, hydroxyethyl starch, pullulan, methylethyl starch, carboxymethyl starch, dextrins, pre-gelatinized starches, and film-forming modified starches; water soluble copolymers such as methacrylic acid and methacrylate ester copolymers, polyvinyl alcohol and polyethylene glycol copolymers, polyethylene oxide and polyvinylpyrrolidone copolymers; and derivatives and combinations thereof. In embodiments wherein the modified release coating is applied via an aqueous polymer it may be desirable to add a thickening agent to modify the viscosity during dipping. Suitable thickening agents include but are not limited to gelatin, gellan gum, carageenan, iota carageenan, kappa carageenan, lambda carageenan, xanthan gum, guar gum, tara gum, maltodextrin, chitin, cyclodextrin, pectin, sodium carboxymethylcellulose, gelling starches, and microcrystalline cellulose. The thickener may be added from about 0.1 percent to about 10 percent by weight of the dried dipped portion.

In certain embodiments of the invention, the dipped portion comprises gelatin for use as a thickener. Gelatin is a natural, thermogelling polymer. It is a tasteless and colorless mixture of derived proteins of the albuminous class which is ordinarily soluble in warm water. Two types of gelatin—Type A and Type B—are commonly used. Type A gelatin is a derivative of acid-treated raw materials. Type B gelatin is a derivative of alkali-treated raw materials. The moisture content of gelatin, as well as its Bloom strength, composition and original gelatin processing conditions, determine its transition temperature between liquid and solid. Bloom is a standard measure of the strength of a gelatin gel, and is roughly correlated with molecular weight. Bloom is defined as the weight in grams required to move a half-inch diameter plastic plunger 4 mm into a 6.67% gelatin gel that has been held at 10° C. for 17 hours. In a preferred embodiment, the flowable material is an aqueous solution comprising 20% 275 Bloom pork skin gelatin, 20% 250 Bloom bone gelatin, and approximately 60% water.

In one embodiment the dipped coating portion comprises at least one pH dependent polymer. Suitable pH dependent polymers for use in the dipped coating portion include but are not limited to include enteric cellulose derivatives, for example hydroxypropyl methylcellulose phthalate, hydroxypropyl methylcellulose acetate succinate, cellulose acetate phthalate; natural resins such as shellac and zein; enteric acetate derivatives such as for example polyvinylacetate phthalate, cellulose acetate phthalate, acetaldehyde dimethylcellulose acetate; and enteric acrylate derivatives such as for example polymethacrylate-based polymers such as poly (methacrylic acid, methyl methacrylate) 1:2, which is commercially available from Rohm Pharma GmbH under the tradename EUDRAGIT S, and poly(methacrylic acid, methyl methacrylate) 1:1, which is commercially available from Rohm Pharma GmbH under the tradename EUDRAGIT L, and the like, and derivatives, salts, copolymers, and combinations thereof.

In one embodiment the dipped coated portion comprises at least one plasticizer. Suitable plasticizers include but are not limited to polyethylene glycol; propylene glycol; glycerin; sorbitol; triethyl citrate; tributyl citrate; dibutyl sebecate; vegetable oils such as castor oil, rape oil, olive oil, and sesame oil; surfactants such as polysorbates, sodium lauryl sulfates, and dioctyl-sodium sulfosuccinates; mono acetate of glycerol; diacetate of glycerol; triacetate of glycerol; natural gums; triacetin; acetyltributyl citrate; diethyloxalate; diethylmalate; diethyl fumarate; diethylmalonate; dioctylphthalate; dibutylsuccinate; glyceroltributyrate; hydrogenated castor oil; fatty acids; substituted triglycerides and glycerides; and the like and/or mixtures thereof. The plasticizer may be added from about 0.5 percent to about 45 percent by weight of the dried dipped portion. In one embodiment, the tablet core or a portion thereof comprises at least one osmagent, an osmotically effective solute or osmotically effective compound that can be blended homogeneously or heterogeneously with the core constituents to form a push member, acting as osmotically effective solutes that are soluble in liquid medium imbibed into the core, and exhibit an osmotic pressure gradient across the semi-permeable shell or shell portion against an exterior liquid medium. Osmagents useful in the present invention include compounds disclosed at col. 8, lines 18-35, of U.S. Pat. No. 5,830,501, which is incorporated herein by reference.

In another embodiment, the core or a portion thereof comprises at least one osmopolymer. The osmopolymer, if employed, exhibits fluid absorbing and or fluid imbibing properties. The osmopolymer comprises a hydrophilic polymer that can interact with water and aqueous biological fluids and then swell or expand to an equilibrium state. The osmopolymer exhibits the ability to retain a significant portion of the imbibed or absorbed fluid. Other osmopolymers include poly(hydroxyalkyl methacrylate) having a molecular weight of 20,000 to 5,000,000; poly(vinylpyrrolidone) having a molecular weight of about 10,000 to 360,000; poly (vinylalcohol) having a low acetate content and lightly crosslinked with glyoxal, formaldehyde, or glutaraidehyde and having a degree of polymerization from 2,000 to 30,000; poly(ethylene oxide) having a molecular weight from 10,000 to 7,800,000; acidic carboxy polymers known as carboxypolymethylene or as carboxyvinyl polymers, a polymer consisting of acrylic acid lightly cross-linked with polyallylsucrose and sold under the trade name CARBOPOL; acidic carboxy polymer having a molecular weight of 200,000 to 6,000,000, including sodium acidic carboxyvinyl hydrogel and potassium acidic carboxyvinyl hydrogel; CYANAMER polyacrylamide; and the like. Representative polymers, used for the purpose of the present invention, are known to those skilled in the art and described, for example, in Scott & Roff, *Handbook of Common Polymers* (published by the Chemical Company Cleveland, Ohio); Ratner & Hoffman, ACS Symposium Series, No. 31, pp. 1 to 36, (1976) (published by the American Chemical Society); and Schact, *Recent Advances in Drug Delivery Systems*, pp. 259 to 278 (published by Plenum Press, N.Y.).

In one embodiment, at least about 30% of the cross-sectional area of the semi-permeable dipped portion, or semi-permeable dipped portion used in dosage forms of this invention is non-striated. In other embodiments, at least about 50% of the cross-sectional area of the semi-permeable dipped portion or semi-permeable dipped portion is non-striated. In yet other embodiments, at least about 80% of the cross-sectional area of the semi-permeable dipped portion or semi-permeable dipped portion is non-striated. As used herein, "non-striated" means homogeneous with respect to appearance, and with respect to the internal structure of the dipped portion when viewed under any magnification and lighting conditions. For example a cross-section of the dipped portion is free of striations, and uniform with respect to refractive properties when observed utilizing a light microscope at a magnification of about 50 to about 400 times.

The costly and lengthy prior art method for building up a semi-permeable coating on tablets and pharmaceutical dosage forms by spray-coating techniques gives rise to a characteristic striated pattern, which is visible in the cross section of such dosage forms or their semi-permeable coatings. These characteristic striations are indicative of the spray-coating process consisting of multiple repetitions of the steps consisting of: (a) application via spraying of coating solution; followed by (b) warm air drying, to a tumbling bed of dosage forms in a revolving coating pan such that numerous layers of coating material are built up as each application of coating material dries to form a layer. The thickness of typical sprayed semi-permeable coatings is about 60 to about 150 microns. The thickness of an individual layer is typically in the range of about 10 microns to about 13 microns.

In one embodiment the thickness of the dipped coating is at least 75 microns, e.g., at least 150 microns.

In one embodiment, the dipped portion is substantially free of pores having a diameter of 0.5-5.0 microns. As used herein, "substantially free" means that the dipped portion has a pore volume of less than about 0.02 cc/g, preferably less than about 0.01 cc/g, more preferably less than about 0.005 cc/g, in the pore diameter range of 0.5 to 5.0 microns. Typical compressed materials have pore volumes of more than about 0.02 cc/g in this pore diameter range. Pore volume, pore diameter and density may be determined using a Quantachrome Instruments PoreMaster 60 mercury intrusion porosimeter and associated computer software program known as "Porowin." The procedure is documented in the Quantachrome Instruments PoreMaster Operation Manual. The PoreMaster determines both pore volume and pore diameter of a solid or powder by forced intrusion of a non-wetting liquid (mercury), which involves evacuation of the sample in a sample cell (penetrometer), filling the cell with mercury to surround the sample with mercury, applying pressure to the sample cell by: (i) compressed air (up to 50 psi maximum); and (ii) a hydraulic (oil) pressure generator (up to 60000 psi maximum). Intruded volume is measured by a change in the capacitance as mercury moves from outside the sample into its pores under applied pressure. The corresponding pore size diameter (d) at which the intrusion takes place is calculated directly from the so-called "Washburn Equation": $d=-(4\gamma(\cos\theta))/P$ where $\gamma$ is the surface tension of liquid mercury, $\theta$ is the contact angle between mercury and the sample surface and P is the applied pressure.

Equipment used for pore volume measurements:
1. Quantachrome Instruments PoreMaster 60.
2. Analytical Balance capable of weighing to 0.0001 g.
3. Desiccator.

Reagents used for measurements:
1. High purity nitrogen.
2. Triply distilled mercury.
3. High pressure fluid (Dila AX, available from Shell Chemical Co.).
4. Liquid nitrogen (for Hg vapor cold trap).
5. Isopropanol or methanol for cleaning sample cells.
6. Liquid detergent for cell cleaning.

Procedure: The samples remain in sealed packages or as received in the dessicator until analysis. The vacuum pump is switched on, the mercury vapor cold trap is filled with liquid nitrogen, the compressed gas supply is regulated at 55 psi, and the instrument is turned on and allowed a warm up time of at least 30 minutes. The empty penetrometer cell is assembled as described in the instrument manual and its weight is recorded. The cell is installed in the low pressure station and "evacuation and fill only" is selected from the analysis menu, and the following settings are employed:

Fine Evacuation time: 1 min.
Fine Evacuation rate: 10
Coarse Evacuation time: 5 min.

The cell (filled with mercury) is then removed and weighed. The cell is then emptied into the mercury reservoir, and two tablets from each sample are placed in the cell and the cell is reassembled. The weight of the cell and sample are then recorded. The cell is then installed in the low-pressure station, the low-pressure option is selected from the menu, and the following parameters are set:

Mode: Low pressure
Fine evacuation rate: 10
Fine evacuation until: 200µ Hg
Coarse evacuation time: 10 min.
Fill pressure: Contact+0.1
Maximum pressure: 50
Direction: Intrusion And Extrusion
Repeat: 0
Mercury contact angle; 140
Mercury surface tension: 480

Data acquisition is then begun. The pressure vs. cumulative volume-intruded plot is displayed on the screen. After low-pressure analysis is complete, the cell is removed from the low-pressure station and reweighed. The space above the mercury is filled with hydraulic oil, and the cell is assembled and installed in the high-pressure cavity. The following settings are used:

Mode: Fixed rate
Motor speed: 5
Start pressure: 20
End pressure: 60,000
Direction: Intrusion and extrusion
Repeat: 0
Oil fill length: 5
Mercury contact angle: 140
Mercury surface tension: 480

Data acquisition is then begun and graphic plot pressure vs. intruded volume is displayed on the screen. After the high pressure run is complete, the low- and high-pressure data files of the same sample are merged.

The dosage forms of the invention provide modified release of one or more active ingredients contained therein. The following non-limiting examples further illustrate the claimed invention.

EXAMPLE 1

Figure 1:
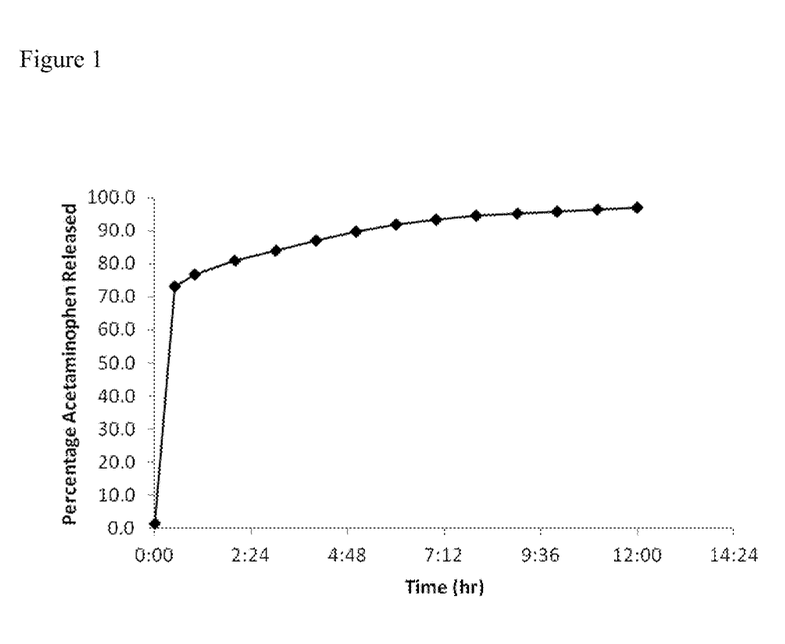
FIG. 1 shows a release profile of the partially coated tablets as prepared according to Example 1.

A tablet dosage form according to the present invention providing immediate release and sustained release during dissolution was manufactured using acetaminophen as model drug as follows. A granulation containing acetaminophen (see Table 1) was compressed into tablets using a Carver Press. The core tablets were then partially coated with methacrylate copolymer solution (see Table 2) using partial dip coating technology to a predetermined length along the longitudinal axis to form a low-permeable coating. Approximately 60 percent of the tablet length (long axis of the tablet) was coated with the polymer coating. The dip coated tablets were then air dried at room temperature for 6-8 hours. The release profiles of these partially coated tablets were evaluated using the USP Type II dissolution apparatus using 0.1M phosphate buffer at pH 6.8. As can be seen by reference to FIG. 1, about 65% of the drug from the uncoated portion of the tablet was released immediately and rest of the drug was released slowly with time from the partially coated portion of the tablet ($t_{90}$=5 hours).

TABLE 1

Acetaminophen Granulation

| Ingredient | mg/tablet |
|---|---|
| Acetaminophen | 500.0 |
| Povidone, USP (29/32) | 16.0 |
| Sodium Starch Glycolate, NF | 10.0 |
| Pregelatinized Starch, NF | 10.0 |
| Colloidal Silicon Dioxide | 3.0 |
| Total | 539.0 |

TABLE 2

Coating Formulation for Partial Dip Coating

| Material | G/Batch | Weight % in Solution |
|---|---|---|
| Methacrylate copolymer* poly(ethyl acrylate, methyl methacrylate, trimethylamino methyl methacrylate chloride) (1:2:01) | 12.5 | 19.23 |
| Triethyl citrate | 2.5 | 3.85 |
| Methanol | 50.0 | 76.92 |
| TOTAL | 65.0 | 100.00 |

*Low-Permeable Grade. Commerically available as Eudragit ® RSPO from Evonik Industries in Piscataway, NJ.

EXAMPLE 2

Figure 2:
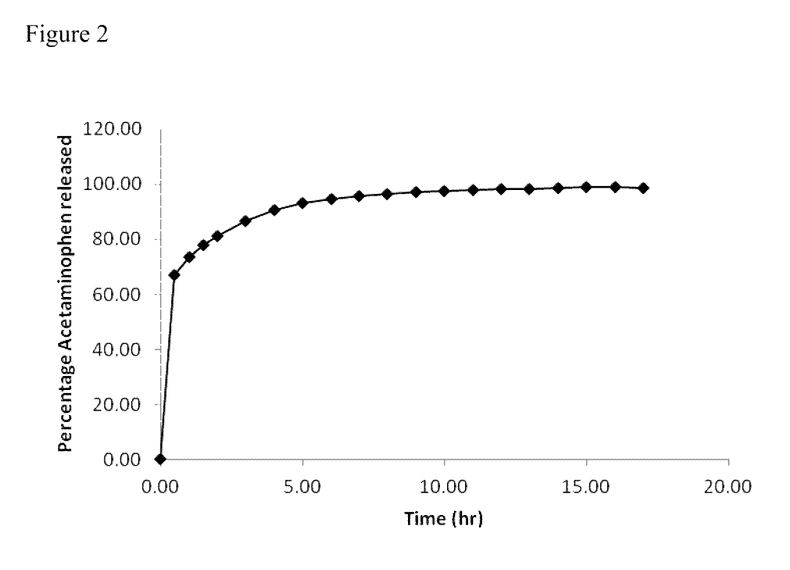
FIG. 2 shows a release profile of the partially coated tablets as prepared according to Example 2.

In a variation of the experiment described in Example 1, acetaminophen core tablets (see Table 3) were partially coated with the methacrylate coating solution (Table 2) on both ends of the tablet leaving an uncoated band in the middle. Approximately 25 percent of the tablet length (long axis of the tablet) was coated with the polymer coating. As seen by reference to FIG. 2, about 65% of the acetaminophen contained in the dosage form was released immediately followed by a slow release of the remaining portion of the drug substance ($t_{90}$=4 hours).

TABLE 3

Acetaminophen Granulation

| Ingredient | mg/tab |
|---|---|
| Acetaminophen | 650.00 |
| Povidone, USP (29/32) | 20.80 |

TABLE 3-continued

Acetaminophen Granulation

| Ingredient | mg/tab |
|---|---|
| Sodium Starch Glycolate, NF | 13.00 |
| Pregelatinized Starch, NF | 13.00 |
| Colloidal Silicon Dioxide | 3.90 |
| Total | 700.70 |

EXAMPLE 3

Figure 3:
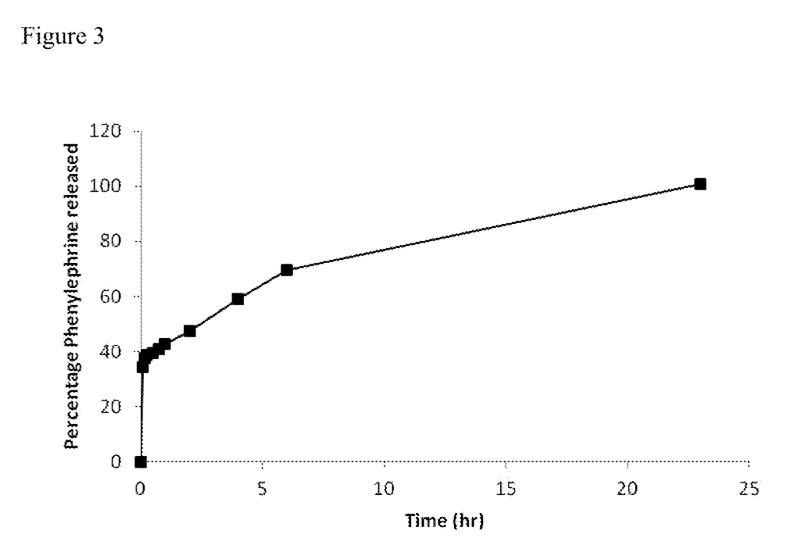
FIG. 3 shows a release profile of the partially coated tablets as prepared according to Example 3.

In another variation to the present invention, a controlled release tablet dosage form containing phenylephrine hydrochloride was manufactured. The core tablet was manufactured using the formula in Table 4 and a Carver Press. Core tablets were partially dip coated to cover 75% of the tablet using the partial dip coating technology as described in Example 1 (Table 2) and tested for drug release. As seen in FIG. 3, approximately 35% of the drug was released immediately from the uncoated portion and the rest of the drug was released slowly (greater than 6 hours).

TABLE 4

Core Formulation of Phenylephrine Hydrochloride Tablet

| Material | mg/tablet | Weight % in Core |
|---|---|---|
| Phenylephrine HCl* | 30.45 | 5.0 |
| Microcrystalline cellulose | 572.46 | 94.0 |
| Magnesium stearate | 6.09 | 1.0 |
| Total | 609.00 | 100.0 |

*Equivalent to 25 mg of phenylephrine base.

EXAMPLE 4

Figure 4:
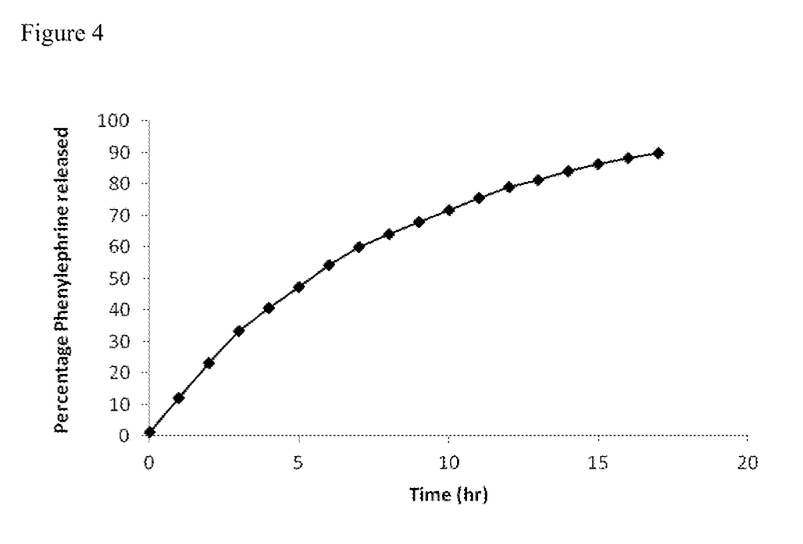
FIG. 4 shows a release profile of the partially coated tablets as prepared according to Example 4.

In another variation to the invention, the core tablets from Example 3 were partially dip coated with low-permeable polymer (Table 2) on one side and a semi-permeable polymer (Table 5) on the other side using partial dip coating technology. Approximately 25 percent of the tablet length (long axis of the tablet) was coated with the semi-permeable polymer coating, and approximately 75 percent of the tablet length was coated with the low permeable polymer coating. The release profile (FIG. 4) showed a sustained release of the drug substance over a period of 20 hours ($t_{90}$=18 hr) without an initial immediate release or burst.

TABLE 5

Formulation for Semi-permeable Coating

| Material | G/Batch | Weight % in Solution |
|---|---|---|
| Methacrylate copolymer* (poly (ethyl acrylate, methyl methacrylate, trimethylaminoethyl-methacrylate chloride)(1:2:02) | 12.5 | 19.23 |
| Tri Ethyl Citrate | 2.5 | 3.85 |
| Methanol | 50.0 | 76.92 |
| TOTAL | 65.0 | 100.00 |

*High-permeable grade. Commerically available as Eudragit ® RLPO from Evonik Industries in Piscataway, NJ.

EXAMPLE 5

Figure 5:
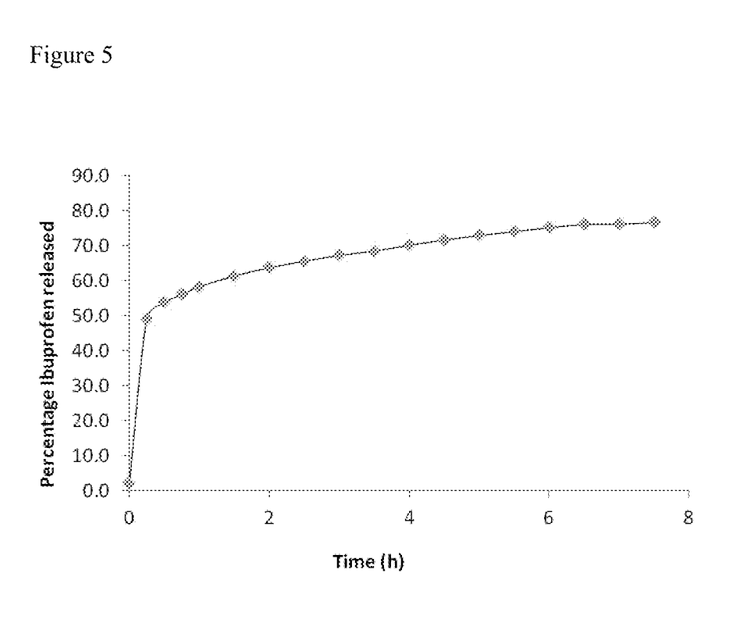
FIG. 5 shows a release profile of the partially coated tablets as prepared according to Example 5.

A dosage form according to the present invention providing controlled release of ibuprofen was manufactured. The formula of the core with 400 mg of active is given in Table 6. To produce the final dosage form, dip coating of the tablets was performed by following the general procedure described in Example 1 using the coating solution composition provided in Table 7. This coating solution is based on an aqueous based polymeric dispersion. Core tablets were dip coated up to 50-60% of the length of the tablet. The release profile of the dosage form prepared according to this example was measured using a USP type II apparatus in 0.1M phosphate buffer at pH 6.8. As seen in FIG. 5, there was an immediate release of active (50%) followed by sustained release of active over 7.5 hours (>75% in 7.5 hr).

TABLE 6

Ibuprofen Granulation

| Description | mg/tablet | weight % |
| --- | --- | --- |
| Common Granulation: | | |
| Ibuprofen USP | 400.00 | 64.65 |
| Corn Starch NF | 165.00 | 26.67 |
| Pregelatinized Starch NF | 22.00 | 3.56 |
| Colloidal Silicon Dioxide NF | 2.00 | 0.32 |
| Extra Granular: | | |
| Corn Starch NF | 25.00 | 4.04 |
| Colloidal Silicon Dioxide NF | 1.20 | 0.19 |
| Stearic Acid NF | 3.50 | 0.57 |
| TOTAL | 618.70 | 100.00 |

TABLE 7

Aqueous-Based Coating Solution

| Ingredient | Weight (g) |
| --- | --- |
| 30% aqueous dispersion of a low permeability methacrylate copolymer poly(ethyl acrylate, methyl methacrylate, trimethylamino methyl methacrylate chloride) (1:2:01)* | 46.0 |
| Gelatine 275 Bloom | 1.5 |
| Tri Ethyl Citrate, NF. | 2.50 |
| Total | 50 |

*Commerically available as Eudragit ® RS 30D from Evonik Industries in Piscataway, NJ.

Figure 6A:
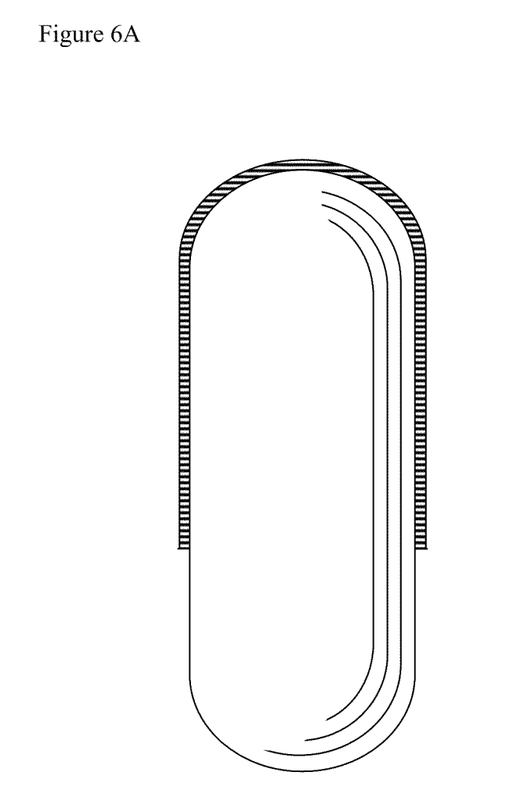
FIG. 6A shows one-sided partial coated tablet with very low-permeable coating.
Figure 6B:
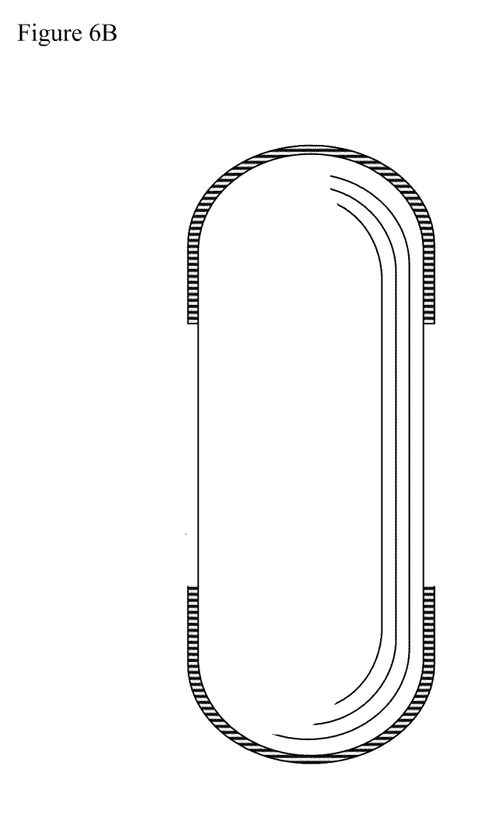
FIG. 6B shows two-sided partial coated tablet with very low-permeable coating.
Figure 6C:
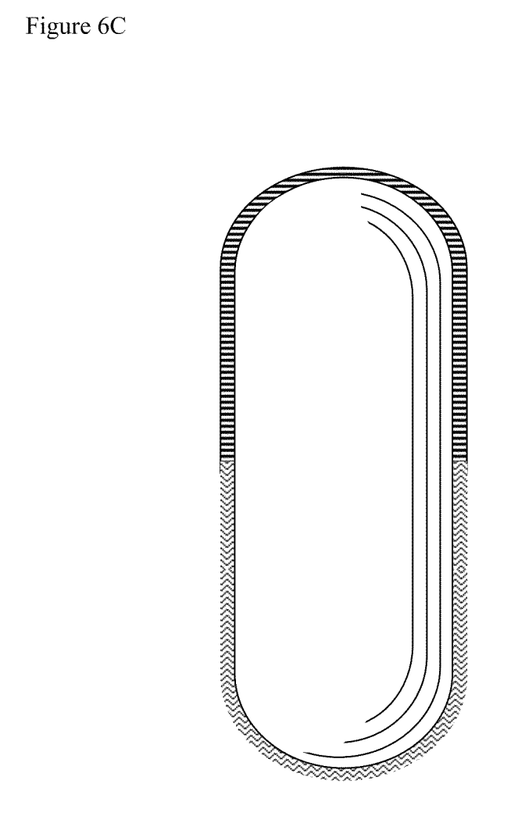
FIG. 6C shows partial coated tablet with one side semi-permeable coating and other side very low-permeable coating.

FIGS. 6A to 6C are illustrations showing dosage forms of the invention. FIG. 6A shows one-sided partial coated tablet with very low-permeable coating. FIG. 6B shows two-sided partial coated tablet with very low-permeable coating. FIG. 6C shows partial coated tablet with one side semi-permeable coating and other side very low-permeable coating.

Although only preferred embodiments of the invention are specifically described above, it will be appreciated that modifications and variations of the invention are possible without departing from the spirit and intended scope of the invention.

The invention claimed is:

1. A method of preparing two or more customized release dosage forms, comprising:
   a. compressing two or more single cores, wherein said two or more single cores are to be used to prepare at least a first dosage form and a second dosage form, wherein each of said two or more single cores is the only core in the first dosage form and the second dosage form, respectively, wherein each of said two or more single cores is non-striated, wherein each of said two or more single cores has a length and a width, wherein each of said two or more single core's length is greater than its width, and wherein each of said two or more single cores comprises at least one active ingredient; and
   b. employing a dipping process to partially coat at least one surface portion of each of the two or more single cores with a modified release coating,
   wherein the length of the coating on the long (i.e., latitudinal) axis of a first of said two or more single cores differs from the length of the coating on the long axis of a second of said two or more single cores in accordance with a desired release rate of the active ingredient from the first dosage form and the second dosage form, respectively, wherein a desired release rate of said first dosage form differs from a desired release rate of said second dosage form; and wherein the customized release dosage forms do not comprise shells.

2. The method of claim 1, wherein the active ingredient is released in a first order manner.

3. The method of claim 1, wherein a first portion of active ingredient is released in an immediate release manner and a second portion of active ingredient is released in a modified release manner.

4. The method of claim 3, wherein the first portion of active ingredient is released from an uncoated portion of the single core, and wherein the second portion of active ingredient is released from a coated portion of the single core.

5. The method of claim 1, wherein the active ingredient is acetaminophen.

6. The method of claim 1, wherein the active ingredient is phenylephrine hydrochloride.

7. The method of claim 1, wherein the active ingredient is ibuprofen.

8. The method of claim 1, further comprising:
   substantially covering the single core with a first coating prior to step b.

9. The method of claim 1, wherein the active ingredient is released in a modified release manner selected from the group consisting of pH dependent release, pH independent burst release, and zero order release.

10. The method of claim 1, comprising employing a polymer coating in the dipping process.

11. The method of claim 10, comprising dispersing said coating in an aqueous medium upon dipping.

12. The method of claim 11, wherein the aqueous medium is selected from an aqueous solution and an aqueous dispersion.

13. The method of claim 10, comprising dispersing said polymer coating in an organic solvent solution upon dipping.

14. The method of claim 1, wherein the compression step comprises multiple steps.

15. The method of claim 1, wherein more than one portion is dip coated.

16. The method of claim 1, wherein the modified release coating comprises poly(ethyl acrylate, methyl methacrylate, trimethylaminoethyl methacrylate chloride) (1:2:0.02).

17. The method of claim 1, wherein the modified release coating comprises triethyl citrate.

* * * * *